United States Patent [19]

Umezawa et al.

[11] Patent Number: 4,550,159
[45] Date of Patent: Oct. 29, 1985

[54] ANTHRACYCLINE COMPOUNDS

[75] Inventors: Hamao Umezawa; Tomio Takeuchi; Masa Hamada; Hiroshi Naganawa, all of Tokyo; Tsutomu Sawa, Ayase; Takeshi Uchida, Yokohama; Masaya Imoto, Urawa, all of Japan

[73] Assignee: Microbial Chemistry Research Foundation, Tokyo, Japan

[21] Appl. No.: 545,137

[22] Filed: Oct. 25, 1983

[30] Foreign Application Priority Data

Nov. 2, 1982 [JP] Japan .................. 57-192727

[51] Int. Cl.⁴ ............ A61K 31/71; C07H 15/24; C12P 19/56
[52] U.S. Cl. .................. 536/6.4; 514/34; 435/78
[58] Field of Search ............... 424/180, 181; 536/6.4

[56] References Cited

U.S. PATENT DOCUMENTS

| | | | |
|---|---|---|---|
| 4,316,011 | 2/1982 | Oki et al. | 536/6.4 |
| 4,329,339 | 5/1982 | Fujiwara et al. | 536/6.4 |
| 4,373,094 | 2/1983 | Oki et al. | 536/6.4 |
| 4,386,198 | 5/1983 | Oki et al. | 536/6.4 |
| 4,418,192 | 11/1983 | Tanaka et al. | 536/6.4 |
| 4,424,342 | 1/1984 | Oki et al. | 536/6.4 |

Primary Examiner—Johnnie R. Brown
Attorney, Agent, or Firm—Ladas & Parry

[57] ABSTRACT

An anthracycline compound, ditrisarubicin, of the formula:

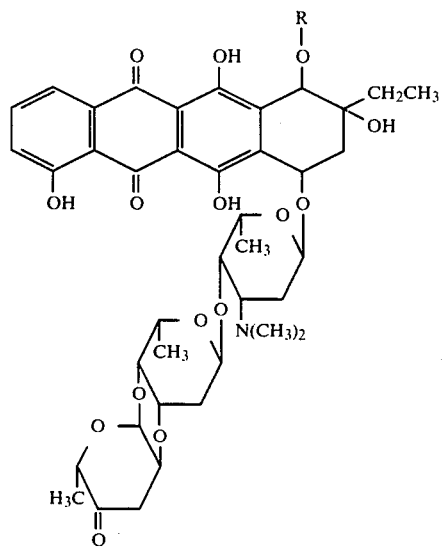

wherein R represents one of the following substituents (A), (B), and (C):

(Abstract continued on next page.)

-continued

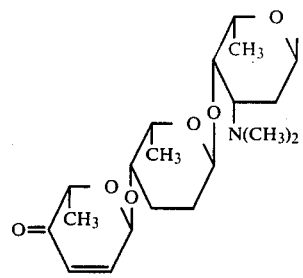
(C)

-continued

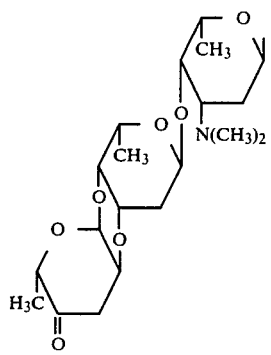
(B)

is produced by a process which comprises cultivating a strain of Streptomyces in a suitable culture medium under aerobic conditions, said strain having the ability to produce the anthracycline compound, ditrisarubicin, and then recovering the anthracycline compound, ditrisarubicin, from the cultured medium. This ditrisarubicin, or an acid addition salt of the ditrisarubicin, can be contained as the active ingredient in antitumor agents and in pharmaceutical compositions for treatment of infections induced by gram-positive microorganisms, whereby good results are attainable.

4 Claims, 9 Drawing Figures

ANTHRACYCLINE COMPOUNDS

BACKGROUND OF THE INVENTION

This invention relates to a novel anthracycline compound, a process for the production thereof, and uses thereof. Anthracycline compounds assume an important position in medicine as antibiotics for the control of cancers, and various anthracycline compounds have been proposed so far.

Generally, the physiological activities of chemicals depend greatly on their chemical structures. There has been constant demand, therefore, for anthracycline compounds which differ from conventional ones in terms of the aglycone moiety, saccharide moiety, and substituent.

SUMMARY OF THE INVENTION

This invention meets the above-mentioned demand.

This invention provides an anthracycline compound, ditrisarubicin, expressed by the formula described below, or acid addition salts of the ditrisarubicin.

This invention also provides a process for producing the anthracycline compound, ditrisarubicin, which process comprises aerobically cultivating a ditrisarubicin-producing strain of Streptomyces in a suitable culture medium, and recovering ditrisarubicin from the cultured broth.

This invention further provides antitumor agents which comprise the anthracycline compound, ditrisarubicin, of the formula indicated below, or its acid addition salts as the active ingredient and carriers.

This invention, moreover, provides pharmaceutical compositions for treating infections associated with gram-positive bacteria, the compositions comprising as the active ingredient the anthracycline compound, ditrisarubicin, of the formula indicated below, or its acid addition salts and carriers.

This invention still provides a method for treating tumors in animals, the method comprising administering to an animal in need of such treatment a safe and effective amount of an anthracycline compound, ditrisarubicin, of the formula indicated below, or an acid addition salt thereof.

This invention still further provides a method of treating gram-positive bacterial infections in animals, the method comprising administering to an animal in need of such treatment a safe and effective amount of an anthracycline compound, ditrisarubicin, of the following formula, or an acid addition thereof.

The term "animal" herein includes humans and lower animals.

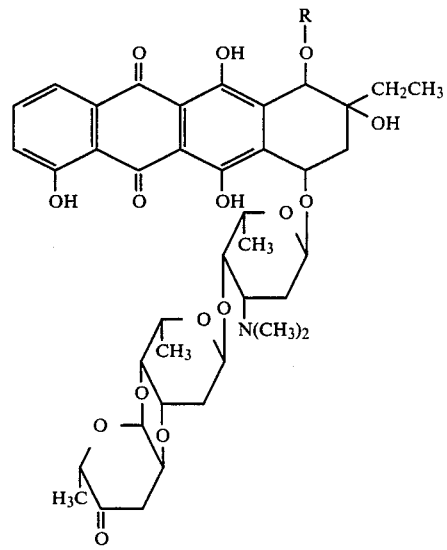

wherein R represents one of the following substituents (A) to (C):

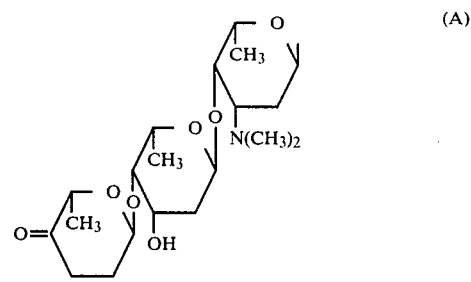

(A)

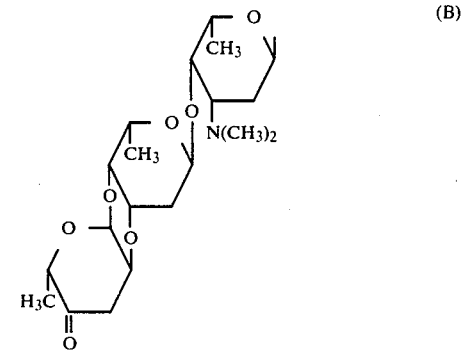

(B)

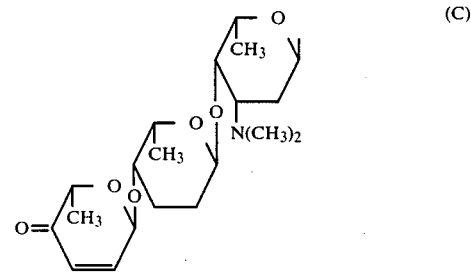

(C)

BRIEF DESCRIPTION OF THE DRAWINGS

In the drawings:

In FIGS. 1, 4 and 7, the curve 1 shows the ultraviolet/visible absorption spectrum of the ditrisarubicin in methanol, the curve 2 shows the ultraviolet/visible absorption spectrum of the ditrisarubicin in 0.1N HCl-90% methanol, and the curve 3 shows the ultraviolet/visible absorption spectrum of the ditrisarubicin in 0.1N NaOH-90% methanol.

DETAILED DESCRIPTION OF THE INVENTION

Figure 1:
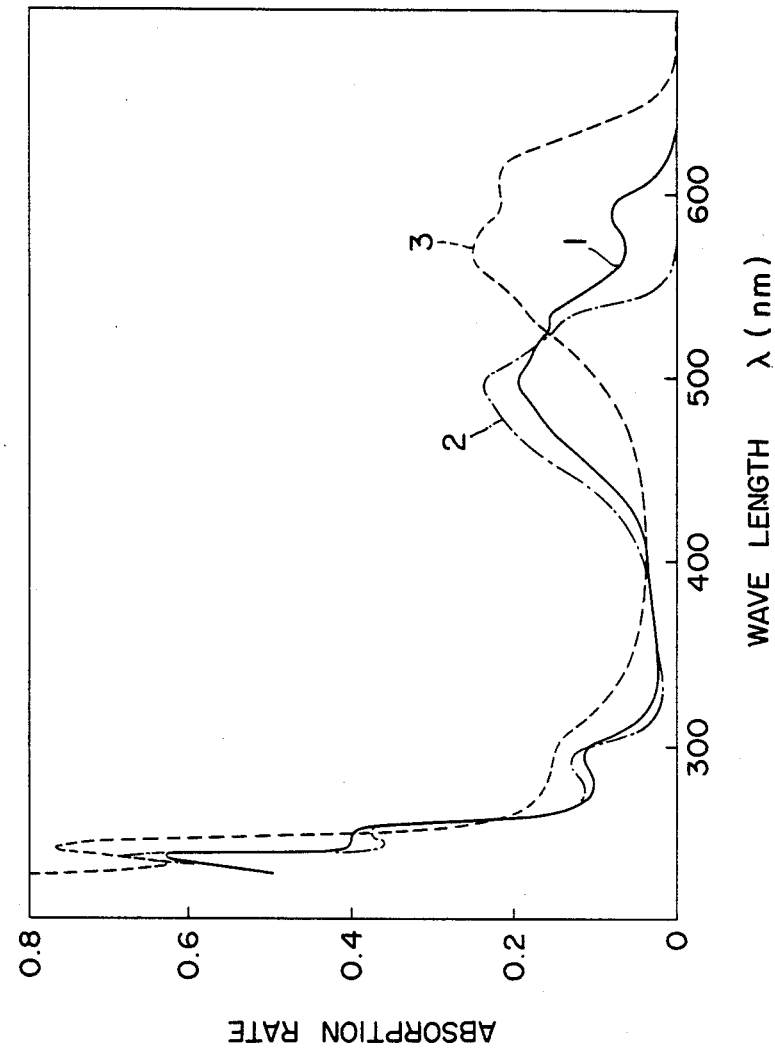
FIG. 1 is the ultraviolet/visible absorption spectrum of ditrisarubicin A in methanol (concentration in methanol: 20 μg/ml)

1. Anthracycline compound, ditrisarubicin (1) Type and chemical structure

The anthracycline compound, ditrisarubicin, according to this invention has a chemical structure as expressed by the above formula. In the formula, the substituent R comes in the three types, (A), (B) and (C). The three types of ditrisarubicin corresponding to these three substituents are called ditrisarubicin A, ditrisarubicin B and ditrisarubicin C, respectively. It should be understood, therefore, that "ditrisarubicin" in the present invention refers to one of ditrisarubicins A, B and C, or a mixture of two or more of these ditrisarubicins.

Ditrisarubicin has a dimethylamino group in its saccharide moiety, and thus can form acid addition salts. Acids to form salts upon addition reaction with ditrisarubicin include hydrohalogenic acids such as hydrochloric acid, sulfuric acid, and tartaric acid.

(2) Determination of chemical structure

Ditrisarubicins A, B and C were each dissolved in 0.1N hydrochloric acid, and heated for 30 minutes at 85° C. for hydrolysis, and extracted with chloroform to obtain a red aglycone. The Rf value on a silica gel plate, mass spectrum, nuclear magnetic resonance spectrum, and ultraviolet/visible absorption spectrum identified the resulting aglycone as β-rhodomycinone in every case of ditrisarubicins A, B and C.

The water-soluble portion obtained after hydrolysis was neutralized with silver carbonate, and developed with an n-butanol-acetic acid-water (4:1:1) solvent mixture on a silica gel plate to examine its saccharidal composition. The constituent saccharides were determined by spraying p-anisaldehyde-sulfuric acid over the silica gel plate after development, heating the plate for 5 minutes at 80° C., and comparing the colors and Rf values of the colored spots with those of standard samples. The results are shown in Table 1.

TABLE 1

| Composition | Proportions of the constituent saccharides (moles) | | |
|---|---|---|---|
| | Ditrisarubicin A | Ditrisarubicin B | Ditrisarubicin C |
| Rhodosamine | 2 | 2 | 2 |
| 2-Deoxyfucose | 2 | 2 | 1 |
| Rhodinose | 0 | 0 | 1 |
| Cinerulose A | 1 | 0 | 0 |
| Cinerulose B | 1 | 2 | 1 |
| Aculose | 0 | 0 | 1* |

Note*: Confirmed by the nuclear magnetic resonance spectrum.

Each of ditrisarubicins A, B and C was catalytically reduced for 30 minutes at room temperature with 5% Pd/BaSO$_4$ as a catalyst, whereby a trisaccharide composed of cinerulose B, 2-deoxyfucose and rhodosamine was released. A fresh red glycoside obtained by this reaction was separated on a silica gel plate, and extracted. The extract was heated for 30 minutes at 85° C. in the presence of 0.1N hydrochloric acid to hydrolyze the same. This procedure revealed the following proportions (moles) of saccharides to constitute the respective ditrisarubicins.

TABLE 2

| Constituents | Ditrisarubicin A | Ditrisarubicin B | Ditrisarubicin C |
|---|---|---|---|
| γ-Rhodomycinone | 1 | 1 | 1 |
| Rhodosamine | 1 | 1 | 1 |
| 2-Deoxyfucose | 1 | 1 | 0 |
| Rhodinose | 0 | 0 | 1 |
| Cinerulose B | 0 | 1 | 0 |
| Cinerulose A | 1 | 0 | 1 |

Figure 2:
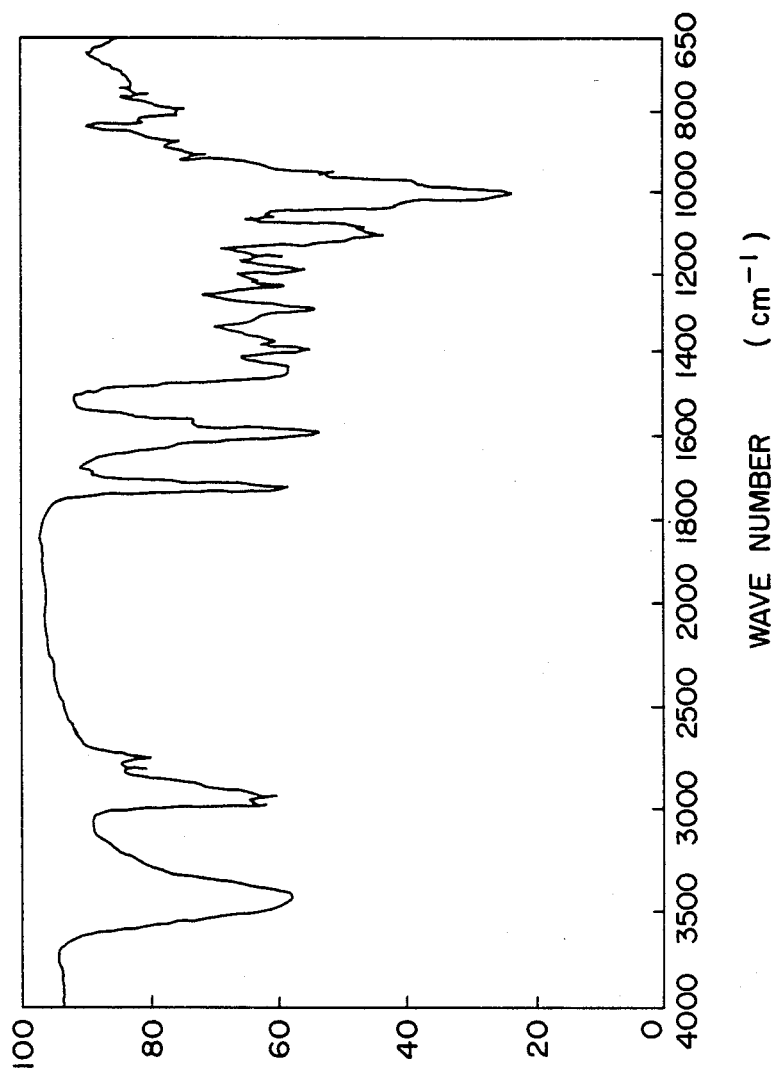
FIG. 2 is the infrared absorption spectrum of ditrisarubicin A tableted in potassium bromide.
Figure 3:
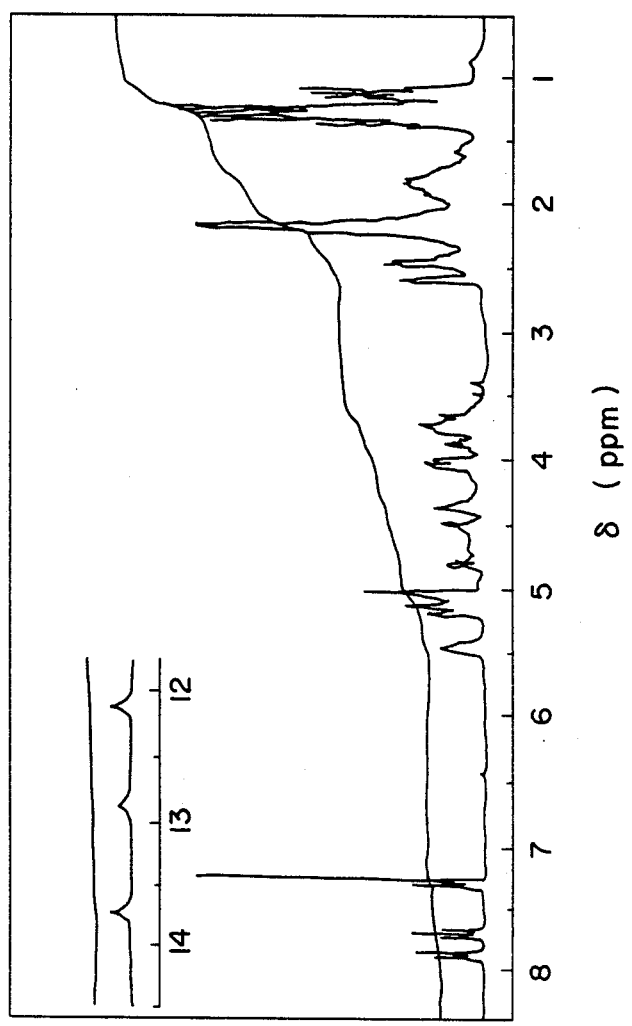
FIG. 3 is the nuclear magnetic resonance spectrum of ditrisarubicin A (250 MHz, in deuterochloroform)
Figure 5:
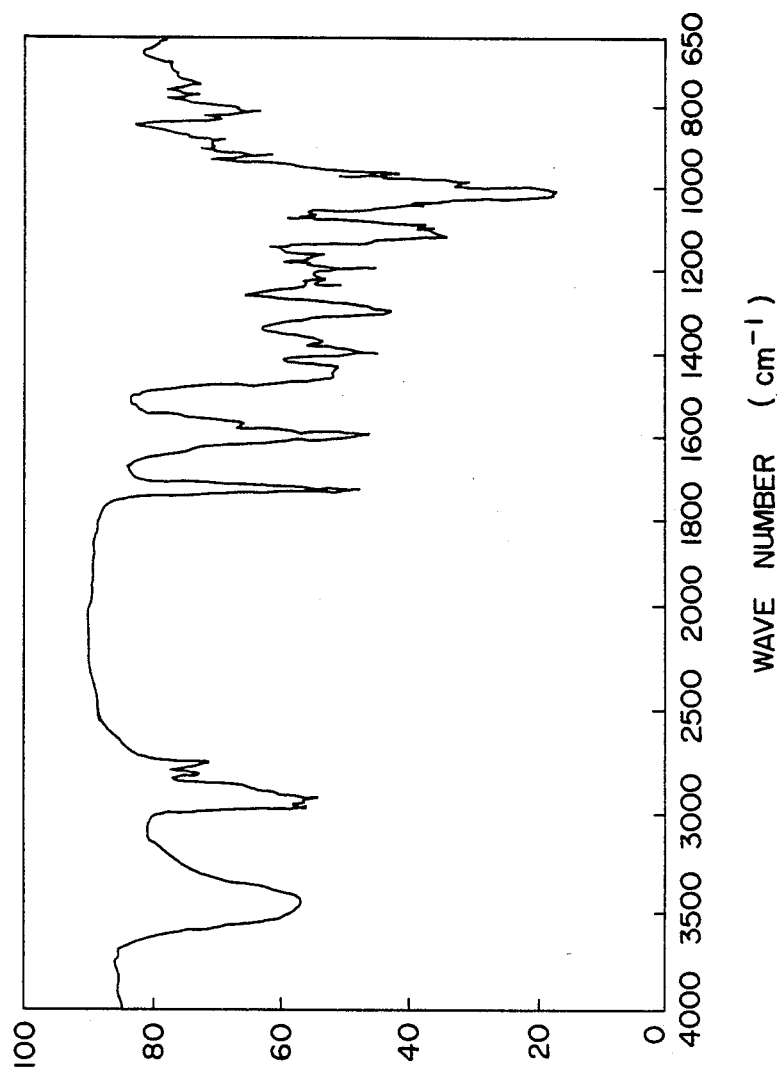
FIG. 5 is the infrared absorption spectrum of ditrisarubicin B tableted in potassium bromide.
Figure 6:
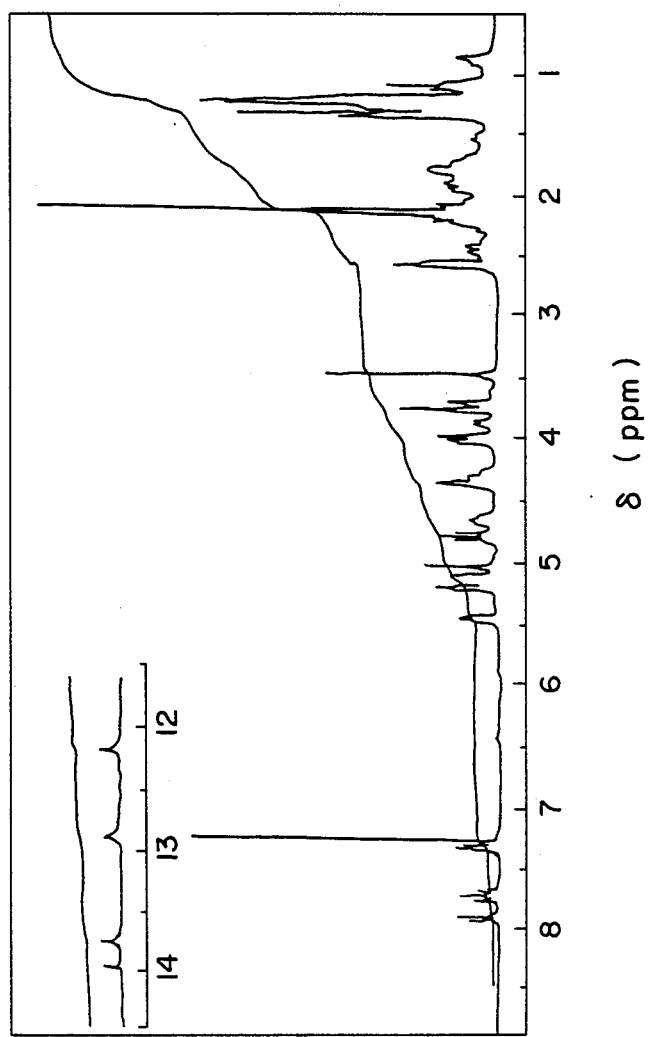
FIG. 6 is the nuclear magnetic resonance spectrum of ditrisarubicin B (250 MHz, in deuterochloroform)
Figure 8:
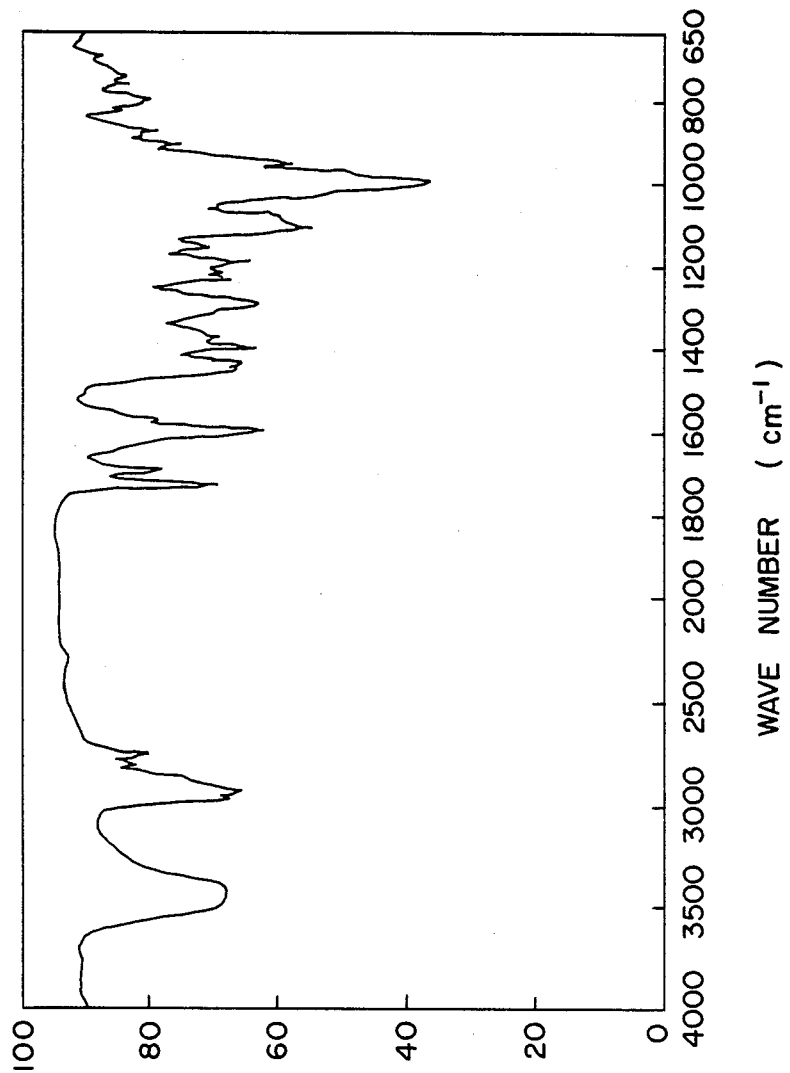
FIG. 8 is the infrared absorption spectrum of ditrisarubicin C tableted in potassium bromide.
Figure 9:
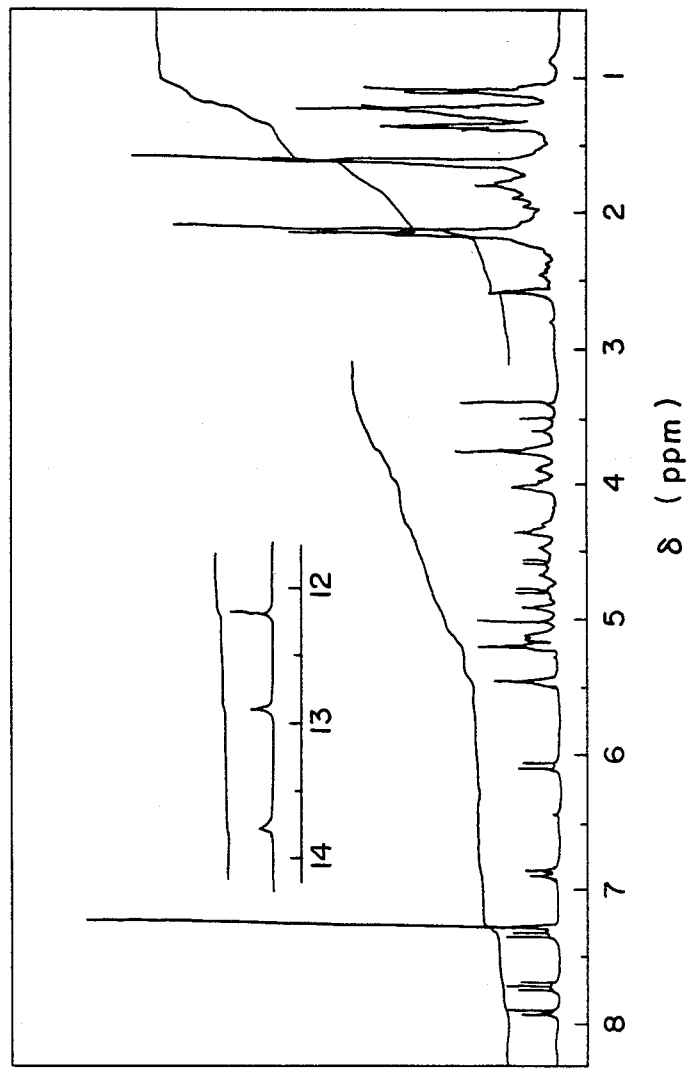
FIG. 9 is the nuclear magnetic resonance spectrum of ditrisarubicin C (250 MHz, in deuterochloroform).

The above results, the NMR spectra (FIGS. 3, 6 and 9) and infrared absorption spectra (FIGS. 2, 5 and 8) of the chemicals of the present invention, and their molecular weights determined by the mass spectra confirmed that ditrisarubicins A, B and C have structures as expressed by the aforementioned formulae.

(3) Physicochemical properties of ditrisarubicin A (1) Appearance: Red powder (2) Elemental analysis: Found: C: 60.15, H: 7.28, N: 2.41, O: 30.16; Calcd.: C: 60.90, H: 6.99, N: 2.37, O: 29.75 (For $C_{60}H_{82}N_2O_{22}$).

(3) Molecular weight: 1183.31.

(4) Melting point: 184°–187° C.

(5) Specific rotatory power: $[\alpha]_D^{25} = +119°$ (C: 0.1 in CHCl$_3$).

(6) Ultraviolet and visible absorption spectrum (in methanol): Shown in FIG. 1. Details are given in Table 3.

TABLE 3

| Solvent | $\lambda max(_{1\ cm}^{1\%})$ |
|---|---|
| Methanol (Curve 1) | 234(320), 252(200), 290(58), 496(100), 530(81), 588(42) |
| 0.1 N hydrochloric acid-90% methanol (Curve 2) | 234(341), 253(187), 290(66), 495(121), 527(77) |
| 0.1 N sodium hydroxide-90% methanol (Curve 3) | 238(385), 288(92), 567(150), 602(133) |

(7) Infrared absorption spectrum (KBr tablet): Shown in FIG. 2.

(8) Nuclear magnetic resonance spectrum (250 MHz, in deuterochloroform): Shown in FIG. 3.

(9) Solubility: Ditrisarubicin A is soluble in methanol, acetone, ethyl acetate, chloroform, acetonitrile, and dimethyl sulfoxide (DMSO), and sparingly soluble in water, n-hexane and petroleum ether. Ditrisarubicin A is red in methanol, but turns reddish purple in the alkaline condition.

(10) Others: Ditrisarubicin A produces a negative ninhydrin reaction, and does not reduce Fehling's solution. On silica gel plate using various solvent systems, ditrisarubicin A has the Rf values shown in Table 6 given later.

Figure 4:
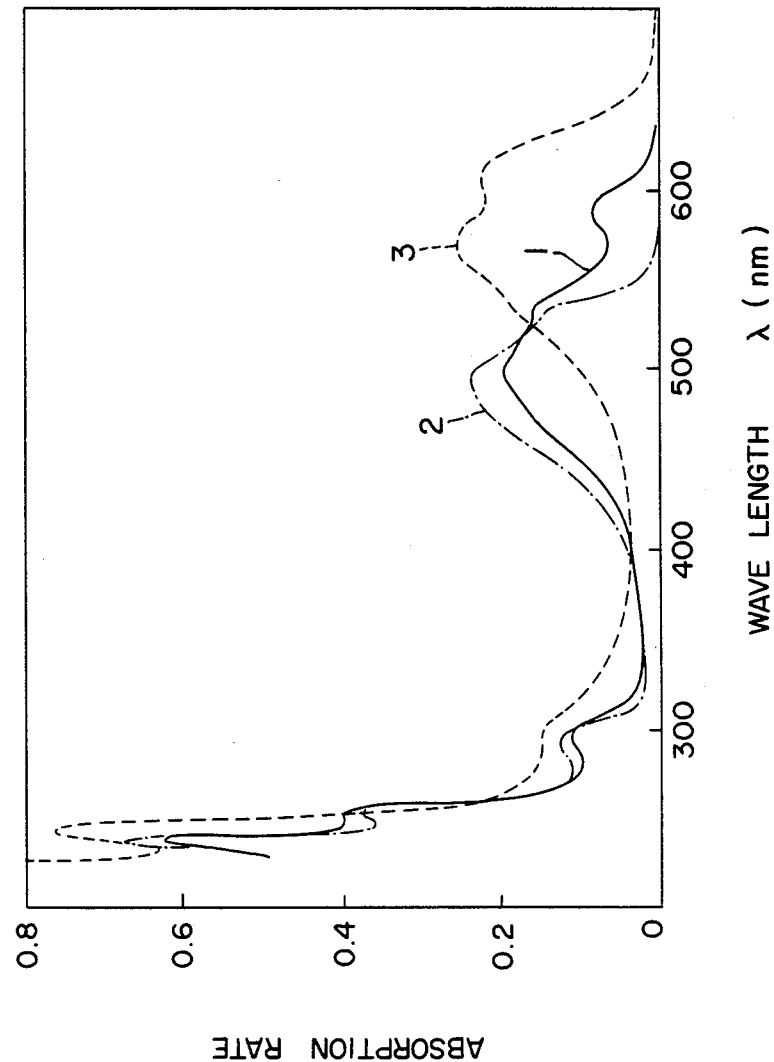
FIG. 4 is the ultraviolet/visible absorption spectrum of ditrisarubicin B in methanol (concentration in methanol: 20 μg/ml)

(4) Physicochemical properties of ditrisarubicin B (1) Appearance: Red powder
(2) Elemental analysis: Found: C: 60.02, H: 7.01, N: 2.30, O: 30.67; Calcd. C: 61.01, H: 6.83, N: 2.37, O: 29.80 (For $C_{60}H_{80}N_2O_{22}$).
(3) Molecular weight: 1181.29.
(4) Melting point: 196°–198° C.
(5) Specific rotatory power: $[\alpha]_D^{25} = +132°$ (C: 0.1, in $CHCl_3$).
(6) Ultraviolet and visible absorption spectrum (in methanol): This spectrum is shown in FIG. 4, and its details are revealed in Table 4.

TABLE 4

| Solvent | $\lambda max(1\%_{1\,cm})$ |
| --- | --- |
| Methanol | 234(320), 252(201), 290(58) |
| (Curve 1) | 496(100), 530(81), 588(42) |
| 0.1 N hydrochloric acid- | 234(341), 253(188), 290(65) |
| 90% methanol (Curve 2) | 495(120), 527(75) |
| 0.1 N sodium hydroxide- | 238(383), 288(90), 567(147) |
| 90% methanol (Curve 3) | 602(130) |

(7) Infrared absorption spectrum (KBr): Shown in FIG. 5.
(8) NMR spectrum (250 MHz, in deuterochloroform): Shown in FIG. 6.
(9) Solubility: Ditrisarubicin B is soluble in methanol, acetone, ethyl acetate, chloroform, acetonitrile and DMSO, and sparingly soluble in water, n-hexane and petroleum ether. Ditrisarubicin B is red in methanol, but changes to reddish purple in the alkaline condition.
(10) Others: Ditrisarubicin B produces a negative ninhydrin reaction, and does not reduce Fehling's solution. The Rf values of ditrisarubicin B on silica gel plate using various solvent systems are revealed in Table 6.

Figure 7:
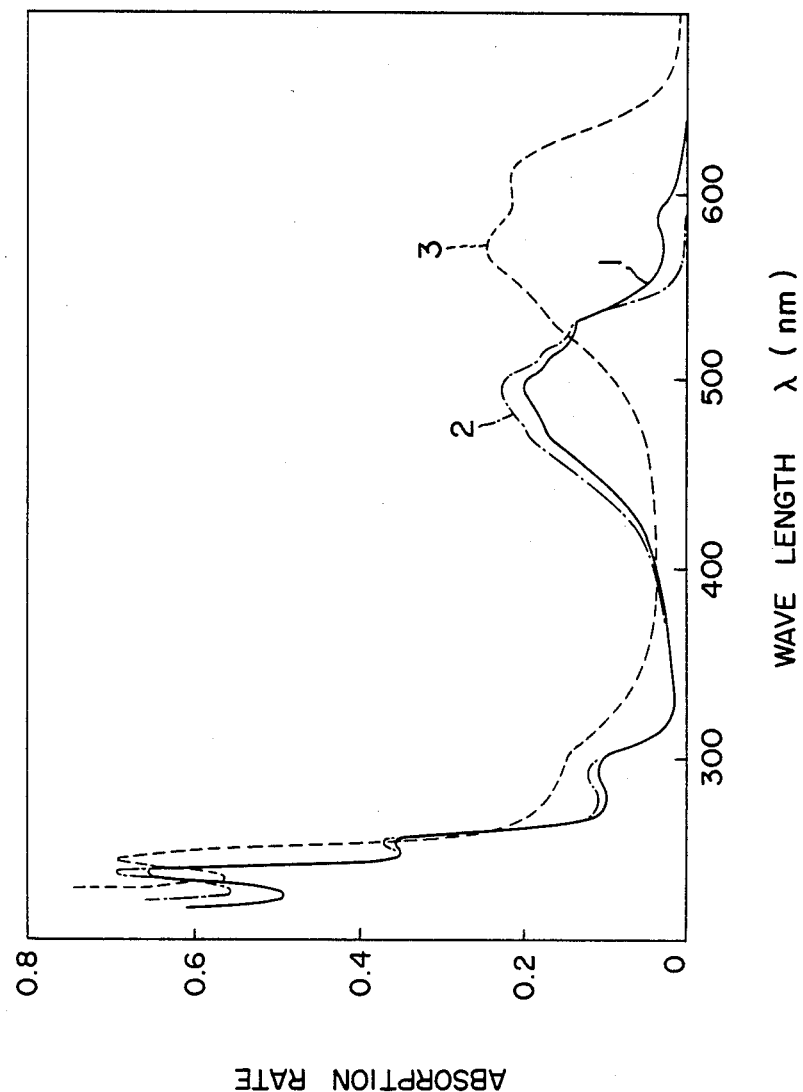
FIG. 7 is the ultraviolet/visible absorption spectrum of ditrisarubicin C in methanol (concentration in methanol: 20 μg/ml)

(5) Physicochemical properties of ditrisarubicin C (1) Appearance: Red powder.
(2) Elemental analysis: Found: C: 61.01, H: 7.15, N: 2.35, O: 29.54; Calcd.: C: 61.84, H: 6.92, N: 2.40, O: 28.83 (For $C_{60}H_{80}N_2O_{21}$).
(3) Molecular weight: 1165.29.
(4) Melting point: 173°–176° C.
(5) Specific rotatory power: $[\alpha]_D^{25} = +167°$ (C: 0.1, in $CHCl_3$).
(6) Ultraviolet and visible absorption spectrum (in methanol): This spectrum is shown in FIG. 7, and is details are given in Table 5.

TABLE 5

| Solvent | $\lambda max(1\%_{1\,cm})$ |
| --- | --- |
| Methanol | 233(330), 253(178), 290(58) |
| (Curve 1) | 495(108), 528(78), 585(35) |
| 0.1 N hydrochloric acid- | 234(347), 254(183), 290(62) |
| 90% methanol (Curve 2) | 495(121), 528(75) |
| 0.1 N sodium hydroxide- | 241(348), 300(75), 568(134) |

TABLE 5-continued

| Solvent | $\lambda max(1\%_{1\,cm})$ |
| --- | --- |
| 90% methanol (Curve 3) | 607(119) |

(7) Infrared absorption spectrum (KBr): Shown in FIG. 8.
(8) NMR spectrum (250 MHz, in deuterochloroform): Shown in FIG. 9.
(9) Solubility: Ditrisarubicin C is soluble in methanol, acetone, ethyl acetate, chloroform, acetonitrile and DMSO, and sparingly soluble in water, n-hexane and petroleum ether. Ditrisarubicin C is red in methanol, but turns reddish purple in the alkaline condition.
(10) Others: Ditrisarubicin C is negative in a ninhydrin reaction, and does not reduce Fehling's solution. The Rf values of ditrisarubicin C on silica gel plate using various solvent systems are shown in Table 6.

TABLE 6

| | Rf Value | | |
| --- | --- | --- | --- |
| Developer | Ditrisarubicin A | Ditrisarubicin B | Ditrisarubicin C |
| Chloroform:methanol (20:1) | 0.74 | 0.88 | 0.79 |
| Chloroform:methanol: acetic acid (20:2:0.1) | 0.63 | 0.79 | 0.65 |
| Chloroform:methanol: conc. ammonium hydroxide (100:5:0.02) | 0.42 | 0.56 | 0.47 |
| Ethyl acetate:methanol (10:1) | 0.09 | 0.32 | 0.11 |

2. Production of ditrisarubicin (1) Outline

The anthracycline compound, ditrisarubicin, has been heretofore obtained only by the cultivation of microorganisms. It may be possible, however, to produce this compound by the synthetic chemical or microbiological modification of analogous compounds, or to produce it by total chemical synthesis.

The cultivation technique uses strains of Streptomyces which have the ability to produce the anthracycline compound, ditrisarubicin. More specifically, we have isolated a strain called Streptomyces cyaneus MG344-hF49 and found that this strain produces ditrisarubicin. Other suitable strains which produce ditrisarubicin can be isolated from the natural environment by customary methods for use in the isolation of antibiotics-producing microorganisms. It may be also possible to increase the ditrisarubicin output by subjecting ditrisarubisin-producing microorganisms (including S. cyaneus MG344-hF49) to treatment with radioactive rays or other treatments.

(2) MG344-hF49

MG344-hF49, a ditrisarubicin-producing strain of Streptomyces discovered by us, will be described in detail below.

(1) Origin and Deposit No.

S. cyaneus MG344-hF49 is an actinomyces isolated from the soil within the site of the Institute of Microbial Chemistry in August 1980. This strain was deposited on June 28, 1982 with the Fermentation Research Institute, Agency of Industrial Science and Technology, Ministry of International Trade and Industry of Japan, where it was assigned the accession number FERM-P No. 6605, which strain now bears the accession number FERM BP-314 under the Budapest Treaty on the International Recognition of the Deposit of Microorganism for the Purposes of Patent Procedure.

(2) Microbiological characteristics

A. Morphology

Microscopically, substrate mycelia of MG344-hF49 are branched and extend aerial hyphae. On the aerial hyphae, hooks or spirals are formed, but no whirls are observed. Chains of mature spores include those having more than 10 spores. The spores range in size from about 0.4 to 0.6×0.8 to 1.0 micron, and their surfaces are spiny.

B. Culture characteristics on various media

In the following disclosure, the standards indicated in square brackets [] to describe colors comply with the Color Harmony Manual issued by the Container Corporation of America.

(a) On sucrose nitrate agar medium (cultured at 27° C.): Growth is dull reddish purple [9 le, Raspberry], and white aerial mycelium develops slightly; purple soluble pigment is produced.

(b) On glucose-asparagine agar medium (cultured at 27° C.): Growth is yellowish red [6 la, Lt Coral Red-6 pc, Paprika], and on the growth light bluish gray [18 ec, Lt Aqua] aerial mycelium develops; reddish soluble pigment is produced.

(c) On glycerol-asparagine agar medium (ISP-5, cultured at 27° C.): Growth is grayish purple [9 lg, Rose Plumn], and on the growth white to grayish white to light bluish gray aerial mycelium develops; no soluble pigment is produced.

(d) On starch-inorganic salts agar medium (ISP-4, cultured at 27° C.): Growth is pale pink, and on the growth white to grayish bluish green [19 ie, Turquoise Green] aerial mycelium develops; pinkish soluble pigment is produced.

(e) On tyrosine agar medium (ISP-7, cultured at 27° C.): Growth is light brown to dark brown, and grayish white to light bluish gray aerial mycelium develops on the growth; slightly brownish soluble pigment is produced.

(f) On nutrient agar medium (cultured at 27° C.): Growth is grayish reddish purple [8 le, Rose Wine], and bright purplish gray aerial mycelium develops on the growth; brown soluble pigment is produced.

(g) On yeast extract-malt extract agar medium (ISP-2, cultured at 27° C.): Growth is grayish reddish purple [9 ne, Raspberry], and white to purplish white to bluish white aerial mycelium develops on the growth; no soluble pigment is produced.

(h) On oatmeal agar medium (ISP-3, cultured at 27° C.): Growth is pale pink to dull purple [10 pc, Fuchsia Purple], and light bluish gray to grayish bluish green [21 li, Dk Jade Gray] aerial mycelium develops on the growth; reddish soluble pigment is produced.

(i) Glycerol-nitrate agar medium (cultured at 27° C.): Growth is grayish purple [9 le, Raspberry], and white aerial mycelium develops slightly on the growth; purple soluble pigment is produced.

(j) Starch agar medium (cultured at 27° C.): Growth is dull grayish reddish purple [7 ½ le, Rose Wine], and no aerial mycelium develops; purple soluble pigment is produced.

(k) On calcium malate agar medium (cultured at 27° C.): Growth is pale purple, and white aerial mycelium develops slightly on the growth; purplish soluble pigment is produced.

(l) On cellulose medium (filter paper-containing synthetic liquid, cultured at 27° C.): No growth is observed.

(m) On gelatin stab culture medium: On simple gelatin medium (cultured at 20° C.), growth is pale yellow, white aerial mycelium slightly develops on the growth, and brown soluble pigment is produced. On glucose peptone gelatin medium (cultured at 27° C.), growth is colorless to pale yellow, pinkish white aerial mycelim develops on the growth, and dark brown soluble pigment is produced.

(n) On skimmed milk medium (cultured at 37° C.): Growth is pink to grayish red, and white aerial mycelium develops slightly on the growth; brownish soluble pigment is produced.

(3) Physiological properties

A. Properties (a) Growth temperatures: Tests for growth were carried out at temperatures of 20°, 24°, 27°, 30°, 37° and 50° C. on glucose-asparagine agar medium. Growth occurred at all these temperatures, except 50° C., and the optimum temperature is considered to be about 30° to 37° C.

(b) Liquefaction of gelatin (15% simple gelatin: cultured at 20° C.; glucose peptone gelatin: cultured at 27° C.):

On simple gelatin medium, liquefaction began after 5 days of cultivation. On glucose peptone gelatin medium, liquefaction was not observed after 2 weeks of cultivation, and slight liquefaction was seen after 3 weeks. The liquefactive strength is considered to be normal to poor for simple gelatin, and poor for glucose peptone gelatin.

(c) Hydrolysis of starch (tested on starch-inorganic salts agar medium, and starch agar medium, each cultured at 27° C.): Hydrolysis was observed after 3 days of cultivation. The hydrolytic strength is normal to poor.

(d) Coagulation and peptonization of skimmed milk (cultured at 37° C.): Coagulation began after 3 days of cultivation, and was completed after 7 days, when peptonization began. The strength is normal.

(e) Production of melanoid pigment (tested to tryptone-yeast extract broth (ISP-1), peptone-yeast extract iron agar medium (ISP-6), tyrosine agar medium (ISP-7), each cultured at 27° C.): Melanoid pigment was produced in all these media.

(f) Utilization of carbon sources (tested on Pridham-Gottlieb agar medium (ISP-9) at 27° C.): L-arabinose, D-xylose, D-glucose, D-fructose, sucrose, inositol, L-rhamnose, raffinose, and D-mannitol were all utilizable for growth.

(g) Dissolution of calcium malate (tested on calcium malate agar medium cultured at 27° C.): Calcium malate was dissolved around the periphery of growth after 7 days of cultivation, but this dissolving action was weak.

(h) Nitrate reduction (tested on 1.0% potassium nitrate-containing peptone water (ISP-8) cultured at 27° C.): Reduction was positive.

B. Conclusion and identification as the new strain

The characteristics described above can be summarized as follows:

The strain MG344-hF49 belongs to Streptomyces, and the cell wall contains 2,6-diaminopimelic acid (each amino group: LL-type). No sporangium is observed, spirals are formed on aerial hyphae, and no whirls are seen. The surface of spores is spiny. Growth on various media is pale pink to grayish reddish purple or yellowish red, and white to bright bluish gray to grayish bluish green aerial mycelium develops on the growth. Purple or reddish soluble pigment is produced. The back of the growth provides a pH indicator, changing from purple to bluish purple or blue on addition of 1N-NaOH. Melanoid pigment production is positive, and proteolytic activity is medium to weak. Degree of hydrolysis of starch is also medium to weak. If these characters are compared with those of known species, the strain MG344-hF49 is most closely related to *Streptomyces cyaneus* [International Journal of Systematic Bacteriology, Vol. 22, page 290, 1972 (Reference 1); Waksman's The Actinomycetes, Vol. 2, page 199, 1961 (Reference 2); Bergey's Manual of Determinative Bacteriology, 7th Ed., page 757, 1957 and 8th Ed., page 822, 1974 (reference 3)].

The properties of the strain MG344-hF49 and *Streptomyces cyaneus* described in the literature will be compared below.

TABLE 7

|  | MG344-hF49 | *Streptomyces cyaneus* ISP 5108 |
| --- | --- | --- |
| Shape of aerial hypha | Spiral | Spiral |
| Surface of spore | Spiny | Spiny |
| Color of aerial mycelium | White to bright bluish gray to grayish bluish green | Pale blue to bluish gray |
| Color of growth | Pale pink to grayish reddish purple | Dark grayish blue to dark grayish purple |
| Soluble pigment | to purplish, or sometimes reddish | to purplish or pluish |
| Production of melanoid pigment | + | + |
| Hydrolysis of starch | + medium to weak | +* weak |
| Coagulation of milk | + | +* |
| Peptonization of milk | + | +* |
| Liquefaction of gelatin | + medium to weak | +* strong |
| Reduction of nitrate | + | —* |
| Utilization of carbon sources |  |  |
| D-glucose | + | + |
| L-arabinose | + | + |
| D-xylose | + | + |
| D-fructose | + | + |
| Sucrose | + | + |
| Inositol | + | + |
| L-rhamnose | + | + |
| Raffinose | + | + |
| D-mannitol | + | + |
| pH indicator | + | + |

*Disclosed in References 2 and 3 mentioned earlier.

As shown in Table 7, the strain MG344-hF49 and *Streptomyces cyaneus* have practically the same properties, except for the reduction of nitrate. The property of reducing nitrates is minimally stable in the case of actinomyces, and it is difficult to distinguish between MG344-hF49 and *Streptomyces cyaneus* on the basis of the difference in the nitrate-reducing property.

Accordingly, MG344-hF49 was considered to be very close to *Streptomyces cyaneus*. Thus, we identified MG344-hF49 as *Streptomyces cyaneus* MG344-hF49.

(3) Cultivation for production of ditrisarubicin

The anthracycline compound, ditrisarubicin, can be prepared by cultivating a ditrisarubicin-producing strain of Streptomyces aerobically in a suitable medium, and recovering the object product from the cultured medium.

Culture media may be those containing any nutritional sources which can be utilized by ditrisarubicin-producing microorganisms. For example, glycerol, glucose, sucrose, maltose, dextrin, starch and fats are useful as carbon sources. Examples of nitrogen sources are organic materials such as soybean flour, cotton seed meal, meat extract, peptone, dry yeast, yeast extract and corn steep liquor, and inorganic materials such as ammonium salts or nitrates (e.g. ammonium sulfate, sodium nitrate and ammonium chloride). If desired, inorganic salts such as sodium chloride, potassium chloride, phosphates, and salts of heavy metals can also be added. In order to prevent foaming during fermentation, suitable anti-foaming agents such as silicone may be added by customary methods. The most suitable method of cultivation is aerobic deep liquid culture which is employed widely for the production output of antibiotics. The suitable cultivation temperature is 20° to 35° C., preferably 25° to 30° C. With this method, the production of ditrisarubicin reaches its maximum after 3 to 7 days of shake culture, or culture under aeration and stirring. There can thus be obtained cultured broths in which ditrisarubicin is accumulated. In the resulting cultured broth a part of the accumulated ditrisarubicin is present in the bacterial cells, but most parts thereof is present in the filtrate of the cultured broth.

Ditrisarubicin can be recovered from such cultured broths by any methods suitable for the recovery. One of the methods is based on extraction. For example, ditrisarubicin in the filtrate of the cultured broth can be recovered by extraction with a water-immiscible solvent for ditrisarubicin (see the foregoing description in the specification), such as ethyl acetate, butyl acetate, chloroform or butanol (a good efficiency of extraction is obtained when the cultured broth filtrate is neutral or weakly basic). Ditrisarubicin in the bacterial cells can be recovered by treating the bacterial cells, which have been obtained by filtration or centrifugation, with ethyl acetate, chloroform, methanol, ethanol, butanol, acetone, methyl ethyl ketone, a hydrochloric acid solution, or an acetic acid solution. It is also possible to subject the cultured broth as such to the above-mentioned extraction step without preliminarily isolating the bacterial cells. The bacterial cells that have been broken may be extracted. Counter-current distribution may be included in the extraction methods.

Another technique for recovering ditrisarubicin from the cultured broth is based on adsorption. The ditrisarubicin-containing liquid material, such as cultured broth filtrate, or the extract obtained by the aforementioned extraction procedure, is subjected to column chromatography, liquid chromatography or the like using a suitable adsorbent, such as activated carbon, alumina, silica gel or Sephadex LH20 (a product of Pharmacia AB). The adsorbent having the object product, ditrisarubicin, adsorbed onto it is eluted to give ditrisarubicin. The resulting ditrisarubicin solution is concentrated to dryness under reduced pressure to obtain a crude form of ditrisarubicin as a red powder.

The crude ditrisarubicin can be purified by performing the aforementioned extraction and adsorption techniques (if desired, in combination) over a desired number of times, followed by recrystallization, if desired. For example, purification can be done by combinations of column chromatography using adsorbents such as silica gel, Sephadex LH-20, a weakly acidic ion exchange resin, Diaion HP-20 (a product of Mitsubishi Chemical Industries, Ltd.) or a gel filter; liquid chromatography using a suitable solvent; counter-current distribution; and thin-layer chromatography. A concrete example of the purification method comprises dissolving a crude powder of ditrisarubicin in a small amount of chloroform, applying the solution to a silica gel column, developing the column with a suitable solvent to elute the respective active ingredients in the separate condition. The desired active fractions are collected and concentrated under reduced pressure. The concentrate is subjected to thin-layer chromatography, and the desired component is scraped off, thereby obtaining a product consisting substantially of a single component. Further purification can be achieved by high-performance liquid chromatography, or crystallization from a suitable solvent.

3. Uses of ditrisarubicin

The anthracycline compound, ditrisarubicin, in accordance with the present invention has carcinostatic activity and antimicrobial activity, and thus, it is useful as a medicine.

(1) Physiological activities

(1) Antitumor activity

To $CDF_1$ mice were intraperitoneally transplanted $1 \times 10^5$ L1210 leukemia cells/mouse as a suspension. After the transplantation, each 0.25 ml of a solution containing the test compound was intraperitoneally injected for 10 days, beginning on the day of transplantation. The mice were observed for 30 days, and the number of days for which the mice were alive (hereinafter referred to as survival days) was counted. The increase of life span (%) compared with the control group consisting of mice administered with physiological saline solution instead of the test compound was calculated from the following equation:

$$\frac{\text{Number of survival days for the test compound}}{\text{Number of survival days for the control group}} \times 100(\%)$$

The results are shown in the following table.

| Dose (mg/kg/day) | Increase of life span (%) | | |
|---|---|---|---|
| | Ditrisarubicin A | Ditrisarubicin B | Ditrisarubicin C |
| 0.25 | 91 | 108 | 114 |
| 0.125 | 119 | 159 | 148 |
| 0.063 | 148 | 148 | 142 |
| 0.031 | 148 | 136 | 182 |
| 0.016 | 136 | 114 | 142 |

(2) Antimicrobial activity

The antimicrobial activity of ditrisarubicin according to the present invention was examined. It is expressed as minimum inhibitory concentration (MIC) determined by the agar dilution method. The results are tabulated below.

| Microorganism | MIC (µg/ml) | | |
|---|---|---|---|
| | Ditrisarubicin A | Ditrisarubicin B | Ditrisarubicin C |
| S. aureus 209 P | <0.2 | <0.2 | <0.2 |
| S. aureus Smith | 0.39 | 0.78 | 0.39 |
| S. aureus MS8710 | <0.2 | 0.39 | <0.2 |
| S. aureus MS9610 | 0.39 | 0.39 | <0.2 |
| M. lysodeikticus IFO 3333 | <0.2 | <0.2 | <0.2 |
| B. subtilis PCI 219 | <0.2 | 0.39 | 0.39 |
| B. cereus ATCC 10702 | 0.39 | 0.39 | 0.39 |
| Coryn. bovis 1810 | 0.78 | <0.2 | <0.2 |
| E. coli NIHJ | 50 | >50 | >50 |
| K. pnuemoniae PCI 602 | 50 | 50 | >50 |
| Sal. typhi T-63 | 50 | >50 | >50 |
| Serr. marcessens | 50 | 50 | 50 |
| Prot. vulgaris OX19 | 50 | 50 | 50 |
| Pseu. aeruginosa A3 | 12.5 | 25 | 25 |

(3) Acute toxicity ($LD_{50}$)

$LD_{50}$ of ditrisarubicin according to the present invention after a single intraperitoneal injection in mice was 5 to 10 mg/kg.

(4) Cytotoxicity

Ditrisarubicin according to the present invention inhibited the growth of cultured cells, and completely inhibited the synthesis of RNA and DNA particularly at low concentrations. The results are shown below.

| L1210 cells | $ID_{50}$ (µg/ml) | | |
|---|---|---|---|
| | Ditrisarubicin A | Ditrisarubicin B | Ditrisarubicin C |
| Growth | 0.0005 | 0.0011 | 0.0007 |
| DNA synthesis | 0.31 | 0.29 | 0.14 |
| RNA synthesis | 0.023 | 0.029 | 0.014 |
| Protein synthesis | 8.5 | inhibition of 23.3% with 10 γ/ml | 3.2 |

(2) Antitumor agents

As described above, the anthracycline compound, ditrisarubicin, according to the present invention was demonstrated to have antitumor activity against tumors.

Accordingly, ditrisarubicin of this invention or its acid-addition salts can be used as pharmaceutical compositions to control or treat tumors.

Ditrisarubicin or its acid-addition salts as antitumor agents can be administered by any route suited to the intended object in dosage forms determined by the route of administration. Usually, ditrisarubicin or its acid-addition salts diluted with pharmaceutically acceptable carriers or diluents are administered as drugs. For example, ditrisarubicin or its acid-addition salts of the present invention can be administered singly or as mixtures with carrier such as maltose or lactose or as non-toxic complexes, such as complexes with deoxyribonucleic acid. The deoxyribonucleic acid may be that extracted from cells of animals or microorganisms, such as calf's thymus, HeLa cells or yeast.

A typical method of administering ditrisarubicin or its acid-addition salts of the present invention is by injection of its or their solution in distilled water for injection use or in physiological saline. Examples of injection include intraperitoneal injection, intramuscular injection, intravenous or intraarterial injection and local administration in case of animals; and intravenous or intraarterial injection, and local administration in man. The dose is determined in view of the results of animal experiments and varying circumstances in such a manner that a total of doses given continuously or intermittently will not exceed a predetermined limit. It goes without saying that specific doses should be varied depending on the mode of administration and situations of patients or animal subjects, such as age, body weight, sex, susceptibility, food, times of administration, concomitant drugs, condition of patients or animals or the severity of their deseases. The optimal doses and the frequency of administration under certain conditions must be determined by experts' optimum dose determination studies on the bases of the abovementioned factors.

(3) Pharmaceutical compositions for treatment of gram-positive bacterial infections As the physiological activity data have demonstrated, ditrisarubicin of this invention is a carcinostatic antibiotic. Specifically, ditrisarubicin or its acid-addition salts exhibit antimicrobial activity against gram-positive bacteria, and thus, can be used as antibiotics effective against staphylococcal infections, diphtheria, pneumonia, etc. The suitable dosage forms and doses can be determined as already explained hereinabove in regard to the use as antitumor agents. The frequency of administration, etc. can be determined with the same care as described previously.

4. Experimental Examples

EXAMPLE 1

(1) Inoculum preparation

A medium used to grow the primary inoculum was prepared according to the following recipe:
Galactose—2%
Dextrin—2%
Bacto soytone (a trade name)—1%
Corn steep liquor—0.5%
Calcium carbonate—0.1%
pH before sterilization—7.4

A loopful of spores from a slant culture of *Streptomyces cyaneus* MG344-hF49 was used to inoculate each of 500 ml. Erlenmeyer flasks each containing 100 ml of the above medium, which had been sterilized. The flasks were placed on a rotary shaker, and the inoculated medium was shake-cultured for 72 hours at 27° C. to prepare an inoculum.

(2) Cultivation

A fermentation medium was prepared according to the following recipe:
Dextrose—3%
Glucose—0.3%
Toast Soya (a trade name for soy bean flour)—2%
Cobalt chloride—0.12 g/l
Calcium carbonate—0.3%

500 ml of inoculum, prepared as described in the step (1) was added to a 30 liter jar fermentor containing 15 liters of the above fermentation medium that had been sterilized. The fermentation was carried out for 90 hours at a temperature of 27° C. at an aeration rate of 15 liters per minute and an agitation speed of 150 r.p.m.

(3) Isolation of ditrisarubicin

The fermented mash from the step (2) was filtered, and the filtrate was adjusted to a pH of 8.0, followed by extraction with 10 liters of butyl acetate. The supernatant of the extract was concentrated to obtain 20 g of an oily material. The oily material was dissolved in a small amount of chloroform, and the solution was adsorbed onto a 100 g silica gel (Kiesel Gel 60, product of E. Merck) column. A gradient elution of the column was carried out using chloroform-methanol with varying mixing proportions. Fractions containing ditrisarubicins A, B and C were collected and concentrated to obtain 175 mg of a ditrisarubicin mixture as a red crude powder.

EXAMPLE 2

100 mg of the red crude powder obtained in Example 1 was dissolved in a small amount of chloroform. The solution was adsorbed onto ten 20×20 cm thin layers (thickness: 0.25 mm) of silica gel (Kiesel Gel 60 $F_{254}$, a product of E. Merck). The thin layers were developed with a 100:5:0.02 mixture of chloroform, methanol and concentrated ammonium hydroxide. Fractions containing ditrisarubicin A, ditrisarubicin B and ditrisarubicin C, respectively, were each scraped off, and eluted from silica gel with the use of a 10:1 mixture of chloroform and methanol. Fractions thus obtained were each concentrated and passed through a Sephadex LH20 column of 1.0×20 cm equilibrated with 1:1 mixture of chloroform-methanol. The column was developed with the same mixture, and the fractions collected were dried under reduced pressure to obtain 13.2 mg of ditrisarubicin A, 25 mg of ditrisarubicin B, and 5.4 mg of ditrisarubicin C, each as a red powder. The resulting products each gave a single fraction on TLC on a silica gel plate and high-performance liquid chromatography using μ-Bondapack $C_{18}$.

What is claimed is
1. An anthracycline compound, ditrisarubicin, of the following formula:

wherein R represents one of the following substituents (A) to (C):
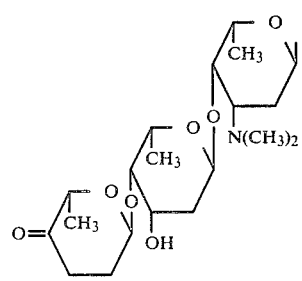
(A)
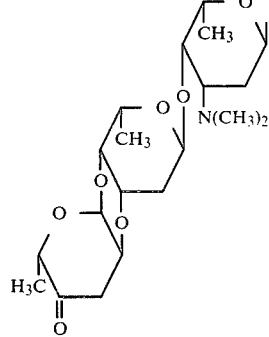
(B)
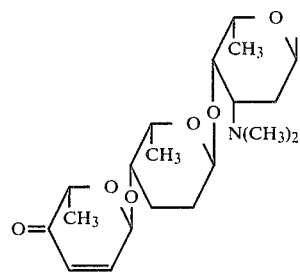
(C)
or an acid addition salt of the ditrisarubicin.
2. An anthracycline compound, ditrisarubicin, as claimed in claim 1 wherein R is said (A).
3. An anthracycline compound, ditrisarubicin, as claimed in claim 1 wherein R is said (B).
4. An anthracycline compound, ditrisarubicin, as claimed in claim 1 wherein R is said (C).
* * * * *